United States Patent [19]

Kijima et al.

[11] 4,062,879

[45] Dec. 13, 1977

[54] PROCESS FOR SYNTHESIS OF COENZYME Q COMPOUNDS

[75] Inventors: Shizumasa Kijima; Isao Yamatsu, both of Tokyo; Norio Minami, Kawasaki; Yuichi Inai, Tokyo, all of Japan

[73] Assignee: Eisai Co., Ltd., Tokyo, Japan

[21] Appl. No.: 725,447

[22] Filed: Sept. 22, 1976

[30] Foreign Application Priority Data

Sept. 29, 1975  Japan .................. 50-116399

[51] Int. Cl.$^2$ .................. C07C 49/73; C07F 5/04
[52] U.S. Cl. .................. 260/396 R; 260/462 C; 260/462 R; 260/613 D
[58] Field of Search .......... 260/396 R, 613 D, 462 R

[56] References Cited

U.S. PATENT DOCUMENTS

| 3,068,295 | 12/1962 | Folker et al. | 260/396 R |
| 3,896,153 | 7/1975 | Sato et al. | 260/396 R |

FOREIGN PATENT DOCUMENTS

| 462,500 | 3/1967 | Japan | 260/396 R |

Primary Examiner—Vivian Garner
Attorney, Agent, or Firm—Blanchard, Flynn, Thiel, Boutell & Tanis

[57] ABSTRACT

A process for synthesizing 2,3-dimethoxy-5-methyl-6-substituted-1,4-benzoquinones having the formula:

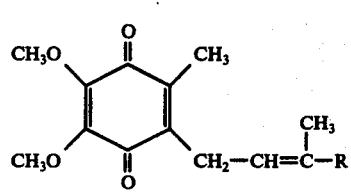

wherein R is

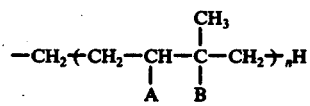

in which $n$ is an integer of 0 to 9, and A and B are hydrogens or taken together form a valence bond, in which 2-methyl-4,5,6-trimethoxyphenol is reacted with boric acid or a reactive derivative thereof to obtain a 2-methyl-4,5,6-trimethoxyphenol ester of boric acid, reacting the resulting ester with an n-prenol or iso-prenol having the formula:

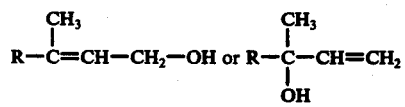

wherein R is as defined above, or a reactive derivative of said n- or iso-prenol, in the presence of a silica-alumina compound, to obtain a 2-methyl-3-substituted-4,5,6-trimethoxyphenol ester of boric acid, and hydrolyzing the thus-obtained ester and treating the resulting 2-methyl-3-substituted 4,5,6-trimethoxyphenol having the formula:

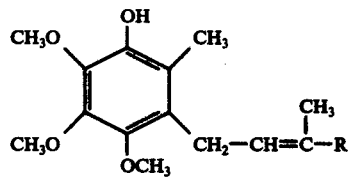

wherein R is as defined above, with an oxidant.

7 Claims, No Drawings

PROCESS FOR SYNTHESIS OF COENZYME Q COMPOUNDS

BACKGROUND OF THE INVENTION

1. Field of the Invention

The present invention relates to a novel process for the synthesis of 2,3-dimethoxy-5-methyl-6-substituted-1,4-benzoquinones having the formula (I):

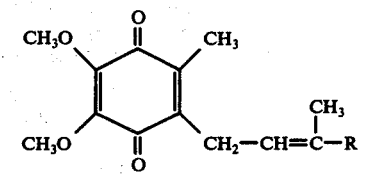

wherein R is

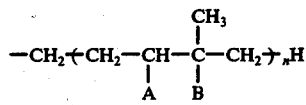

in which $n$ is an integer of 0 to 9, and A and B are hydrogens or A-B together form a direct valence bond between the two carbon atoms to which they are attached.

Compounds of formula (I) are known as coenzymes Q, and especially, 2,3-dimethoxy-5-methyl-6-decaprenyl-1,4-benzoquinone [2,3-dimethoxy-5-methyl-6-(3,7,11,15,19,23,27 31,34,39-decamethyltetracontadecaen-2,6,10,14,18,22,26,30, 34,38-yl)-1,4-benzoquinone] in which A-B is a direct valence bond and $n$ is 9, which is called "coenzyme $Q_{10}$", participates in the electron transport system in living bodies and plays an important role for producing energy. This compound has activities of improving the state of the myocardium in patients suffering from ischemia, increasing the reduced heart beat number and competing with the Na-storage action of aldosterone, and is effective for treating and preventing congestive heart failure, lung congestion, swelling of the liver and angina pectoris.

2. Description of the Prior Art

As known processes for the synthesis of compounds of formula (I), there can be mentioned a method comprising reacting 2,3-dimethoxy-6-methyl-1,4-benzohydroquinone or a 1-monoacyl derivative thereof with an n- or iso-prenol or a reactive derivative thereof, in the presence of an acid catalyst such as a protonic acid, e.g., formic acid, sulfuric acid, hydrochloric acid, phosphoric acid, p-toluene-sulfonic acid or the like, a Lewis acid, e.g., zinc chloride, a boron trifluoride-ether complex or the like, or a mixture of these protonic or Lewis acids, to obtain a corresponding hydroquinone (see Japanese Patent Publications No. 17513/64 and No. 3967/71), and reacting the hydroquinone with an oxidizing agent to convert it to a corresponding benzoquinone (see Japanese Patent Publication No. 17514/64). In such known method, however, because the yield in the condensation step is low, the yield of the intended quinone compound is very low and even the yield of the crude product is about 30% at the highest. Further, each of the acid catalysts that are used in the condensation step is highly corrosive and has a bad effect on the equipment, and metal dissolved out from the acid catalyst contaminates the product. Accordingly, industrial working of this known method involves various disadvantages.

Further, since an acid catalyst such as mentioned above is employed, neutralization, extraction and other post treatments must be conducted for separating the desired product from the reaction mixture, and since the amount of the catalyst used for the reaction is relatively large and the catalyst used must often be discarded after completion of the reaction, the manufacturing cost is increased and environmental pollution is readily caused. Thus, this known method involves various industrial difficulties.

SUMMARY OF THE INVENTION

In accordance with the present invention, there is provided a process for the synthesis of 2,3-dimethoxy-5-methyl-6-substituted-1,4-benzoquinones having the above formula (I), which comprises reacting 2-methyl-4,5,6-trimethoxyphenol with boric acid, or a reactive derivative thereof, to obtain a 2-methyl-4,5,6-trimethoxyphenol ester of boric acid (step 1), reacting the resulting boric acid ester with a n- or iso-prenol having the formula:

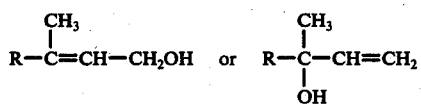

wherein R is

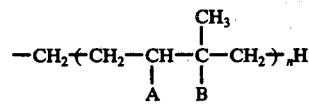

in which $n$ is an integer of 0 to 9, and A and B are hydrogens or A-B forms a direct valence bond between the carbon atoms to which they are attached, or a reactive derivative thereof, in the presence of a silica-alumina compound, to obtain a 2-methyl-3-substituted-4,5,6-trimethoxyphenol ester of boric acid (step 2), and hydrolyzing the thus-obtained boric acid ester to a 2-methyl-3-substituted-4,5,6-trimethoxyphenol having the formula (II):

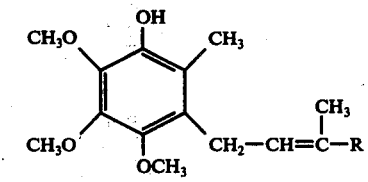

wherein R is as defined above.

and treating the thus-obtained compound with an oxidizing agent to obtain a 2,3-dimethoxy-5-methyl-6-substituted-1,4-benzoquinone having the above formula (I) (step 3).

Production of 2-methyl-4,5,6-trimethoxyphenyl borate in step 1 can be accomplished according to customary methods for the production of boric acid esters, for example, the method disclosed in J. Am. Chem. Soc., 75, 213 (1953).

As the reactive derivative of boric acid, there can be mentioned, for example, borax, boric anhydride, orthoboric acid and metaboric acid.

The stability of the boric acid ester obtained in step 1 to water is very low. Accordingly, it is preferred that the as-prepared ester be immediately transferred to the next step without isolation.

As the n- or iso-prenol or its reactive derivative to be used in step 2, there can be mentioned for example, 3-methylbuten-2-ol-1, 3-methylbuten-1-ol-3, geraniol, linalool, nerol, nerolidol, phytol, isophytol, geranylgeraniol, geranyllinalool, geranylfarnesol, geranylnerolidol, farnesylfarnesol, farnesylnerolidol, geranylgeranylfarnesol, solanesol, decaprenol, isodecaprenol, and halides derived from these alcohols.

As the silica-alumina compound that is present in the reaction mixture, there can be mentioned, for example, clay, active clay, kaolin, natural and synthetic zeolites, silica-alumina silica-alumina-boria and silica-alumina-magnesia. An amount of the silica-alumina compound is from ¼ to 2 times the weight of 2-methyl-4,5,6-trimethoxyphenol to be used as a reactant.

In practicing this reaction in the process of the present invention, it is preferred that there be used a solvent appropriately chosen from the group consisting of aromatic hydrocarbons such as benzene, toluene and xylene, ether type solvents such as diethyl ether, diisopropyl ether and tetrahydrofuran, aliphatic hydrocarbons such as pentane, hexane, heptane, octane, isooctane, petroleum ether and ligroin and ester type solvents such as ethyl acetate.

Hydrolysis of the boric acid ester in step 3 is readily accomplished by simply contacting the boric acid ester obtained in step 2 with water. In general, the hydrolysis is performed by washing the product obtained in step 2 with water.

Oxidation of the phenol of above formula (II) is conducted according to a customary quinone-forming method using a mild oxidant such as silver oxide, lead oxide, ferric chloride, aqueous hydrogen peroxide or the like. For example, the phenol of the above formula (II) can easily be ozidized according to the method disclosed in Japanese Patent Publication No. 17514/64 of Japanese Patent Application Laid-Open Specification No. 49733/73.

It is possible to conduct steps 1 to 3 in a continuous manner. Since the compound of formula (II) is relatively stable, it is possible to isolate and purify the compound of formula (II) and check the degree of completion of the reaction.

The process of the present invention provides the following important advantages in comparison with the above-mentioned conventional methods.

1. Improvement of Yield

In the process of the present invention, because the yield of the condensation step 2 is high, the final intended quinone of formula (I) can be obtained in a high yield. For example, it has been confirmed that pure coenzyme $Q_{10}$ can be obtained in a yield of 65% or higher according to the process of the present invention.

2. Reduction of Number of Steps

A large number of steps are required for obtaining a compound of formula (I) from a compound of formula (II) according to the conventional techniques. For example, the compound of formula (II) is converted to 2,3-dimethoxy-5-methyl-1,4-benzoquinone according to the method disclosed in Japanese Patent Publication No. 28503/74, and the thus-obtained quinone is reduced to 2,3-dimethoxy-5-methyl-1,4-benzohydroquinone, which is monoacylated according to need. Then, the resulting benzohydroquinone or monoacylated product thereof is condensed with an n- or iso-prenol or a reactive derivative thereof to obtain a 2,3-dimethoxy-5-methyl-6-substituted-1,4-benzohydroquinone or a monoacylate thereof (Japanese Patent Publication No. 17513/64 ), and then, the thus-obtained compound is oxidized to obtain the desired product of formula (I) (Japanese Patent Publication No. 17514/64). Thus, according to the conventional techniques, 4 to 5 steps are required for obtaining the desired compounds of formula (I) and complicated operations are included in these steps. In contrast, according to the process of the present invention, the synthesis is accomplished by three steps.

3. Prevention of Corrosion of Equipment and Occurrence of Environmental Pollution In the condensation step 2, an acidic chemical such as zinc chloride, a boron trifluoride-ether complex or the like is used as a condensation catalyst in the prior art methods. Such acidic chemical is highly corrosive and a reaction vessel composed of an anti-corrosive material must be used. Further, when a metal halide or the like is used as a condensation catalyst, metal ions are dissolved out and cause environmental pollution. In the process of the present invention, since these acidic condensation catalysts need not be used at all, none of these disadvantages are brought about.

In view of the foregoing, it will readily be understood that the process of the present invention is very advantageous in comparison with prior art methods.

The present invention will now be described in more detail by reference to the following illustrative example.

EXAMPLE 1

(Synthesis of 2,3-Dimethoxy-5-Methyl-6-Decaprenyl-1,4-Benzoquinone)

a. Synthesis of 2-methyl-3-decaprenyl-4,5,6-trimethoxyphenol

To 30 ml of toluene were added 2 g of 2-methyl-4,5,6-trimethoxyphenol and 6 g of boric acid, and the mixture was refluxed for 2 hours under agitation while removing water formed by the reaction. Then, 15 ml of toluene was distilled from the reaction mixture, and the residue was cooled to 50° C and 35 ml of n-hexane and 20 g of silica-alumina were added thereto. The mixture was heated at 50° to 58° C for 30 minutes under agitation. Under the same conditions a solution of 14 g of decaprenol (having a purity of 94.4%) in 10 ml of n-hexane was added dropwise to the reaction mixture over a period of 40 minutes. The mixture was further heated and agitated for 10 minutes to complete the reaction. After completion of the reaction, the reaction mixture was filtered, and the filtered solids were washed with diethyl ether. The washing liquor was combined with the filtrate, and the organic layer was recovered and washed with water and then with a 10% aqueous solution of sodium hydroxide. The organic solvent layer was recovered and the solvent was distilled therefrom to obtain 16.8 g of a light yellow oily product. A part of the product was sampled and purified by silica gel column chromatography to obtain a standard substance for identification. The purified product was white crystals melting at 43° to 44° C. Elementary analysis values of the purified product as $C_{60}H_{94}O_4$ were as follows:

Calculated: C, 81.95%; H, 10.77%. Found: C, 81.73%, H, 10.61%.

b. Synthesis of 2,3-dimethoxy-5-methyl-6-decaprenyl-1,4-benzoquinone

In 100 ml of ethyl acetate was dissolved 8.4 g of the light yellow oily product obtained in step (a), and 35 g of ferric chloride hexahydrate was added to the solution and the mixture was agitated for 2 hours at room temperature. Then, 100 ml of water was added to the mixture and the resulting mixture was sufficiently shaken. The organic solvent layer was recovered, washed with water and dried with sodium sulfate. The solvent was distilled to obtain 8.3 g of a reddish brown oily product. All of the thus-recovered product was purified by silica gel column chromatography using diethyl ether-n-hexane as an eluting solvent to obtain 5.3 g of a light yellowish orange oily product. The yield was 65.0% based on the decaprenol.

A part of the thus-obtained product was recrystallized from acetone to obtain yellowish orange crystals having a melting point of 49° to 50° C. Results of UV, IR, NMR and MAS spectrum measurements were in agreement with those of a standard substance of 2,3-dimethoxy-5-methyl-6-decaprenyl-1,4-benzoquinone.

The embodiments of the invention in which as exclusive property or privilege is claimed are defined as follows:

1. A process for synthesizing 2,3-dimethoxy-5-methyl-6-substituted-1,4-benzoquinone having the formula

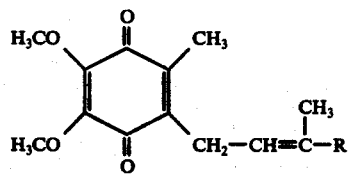

wherein R is

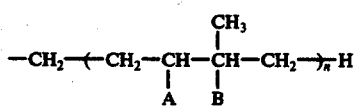

in which n is an integer from zero to 9, and A and B are hydrogens or A-B is a direct valence bond between the carbon atoms to which they are attached, which comprises 1. reacting 2-methyl-4,5,6-trimethoxyphenol with a member selected from the group consisting of borax, boric anhydride, orthoboric acid and metaboric acid to form the corresponding borate,
2. reacting the borate obtained in step (1) with a prenol compound having the formula

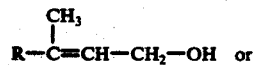

an iso-prenol compound having the formula

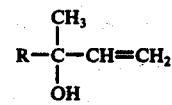

wherein R has the same meaning as defined above, or a corresponding halide derivative thereof, in the presence of a silica-alumina compound, to obtain the 2-methyl-3-substituted-4,5,6-trimethoxyphenyl borate, 3. hydrolyzing the borate obtained in step (2) to obtain a compound having the formula

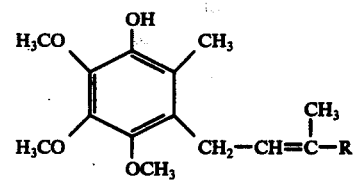

wherein R has the same meaning as defined above and then reacting the latter compound with a mild oxidizing agent to obtain a compound of the first-named formula.

2. A process as claimed in claim 1 in which said prenol compound or said isoprenol compound is selected from the group consisting of 3-methylbuten-2-ol-1, 3-methylbuten-1-ol-3, geraniol, linalool, nerol, nerolidol, phytol, isophytol, geranylgeraniol, geranyllinalool, geranylfarnesol, geranylnerolidol, farnesylfarnesol, farnesylnerolidol, geranylgeranylfarnesol, solanesol, decaprenol, isodecaprenol, and halides thereof.

3. A process as claimed in claim 1 in which said silica-alumina compound is selected from the group consisting of clay, active clay, kaolin, natural and synthetic zeolites, silica-alumina, silica-alumina-boria and silica-alumina-magnesia.

4. A process as claimed in claim 1 in which said mild oxidizing agent is selected from the group consisting of silver oxide, lead oxide, ferric chloride, aqueous hydrogen peroxide and mixtures thereof.

5. A process for synthesizing borates of

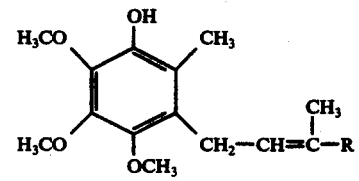

wherein R is

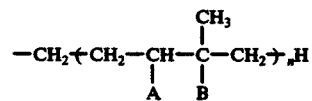

in which n is an integer from zero to 9, and A and B are hydrogens or A-B is a direct valence bond between the carbon atoms to which they are attached.

which comprises 1. reacting 2-methyl-4,5,6-trimethoxyphenol with a member selected from the group consisting of borax, boric anhydride, othoboric acid and metaboric acid to form the corresponding borate, and 2. reacting the borate obtaining in step (1) with a prenol compound having the formula

or an iso-prenol compound having the formula

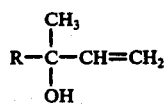

wherein R has the same meaning as defined above, or a corresponding halide derivative thereof
in the presence of a silica-alumina compound to obtain the 2-methyl-3-substituted-4,5,6-trimethoxyphenyl borate.

6. A process as claimed in claim 5 in which said prenol compound or said isoprenol compound is selected from the group consisting of 3-methylbuten-2-ol-1, 3-methylbuten-1-ol-3, geraniol, linalool, nerol, nerolidol, phytol, isophytol, geranylgeraniol, geranyllinalool, geranylfarnesol, geranylnerolidol, farnesylfarnesol, farnesylnerolidol, geranylgeranylfarnesol, solanesol, decaprenol, isodecaprenol, and halides thereof.

7. A process as claimed in claim 5 in which said silica-alumina compound is selected from the group consisting of clay, active clay, kaolin, natural and synthetic zeolites, silica-alumina silica-alumina-boria and silica-alumina-magnesia.

UNITED STATES PATENT AND TRADEMARK OFFICE
CERTIFICATE OF CORRECTION

PATENT NO. : 4 062 879
DATED : December 13, 1977
INVENTOR(S) : Shizumasa Kijima, Isao Yamatsu, Norio Minami and Yuichi Inai It is certified that error appears in the above-identified patent and that said Letters Patent are hereby corrected as shown below:

Column 6, line 39; change "silia-" to ---silica- ---.

Column 7, line 1; change "othoboric" to ---orthoboric---.

Column 8, line 17; after "silica-alumina" insert a comma (,).

Signed and Sealed this

Fourth Day of April 1978

[SEAL]

Attest:

RUTH C. MASON
Attesting Officer

LUTRELLE F. PARKER
Acting Commissioner of Patents and Trademarks